US008870744B2

(12) United States Patent
Hjelle et al.

(10) Patent No.: US 8,870,744 B2
(45) Date of Patent: *Oct. 28, 2014

(54) CARDIAC SUPPORT DEVICE DELIVERY TOOL WITH INDEPENDENTLY MOVABLE ARMS

(75) Inventors: Aaron J. Hjelle, Champlin, MN (US); Paul Andrew Pignato, Stacy, MN (US); Robert G. Walsh, Lakeville, MN (US); William E. Cohn, Houston, TX (US); Ann Margaret Thomas, Plymouth, MN (US)

(73) Assignee: Mardil, Inc., Plymouth, MN (US)

( * ) Notice: Subject to any disclaimer, the term of this patent is extended or adjusted under 35 U.S.C. 154(b) by 48 days.

This patent is subject to a terminal disclaimer.

(21) Appl. No.: 12/764,508

(22) Filed: Apr. 21, 2010

(65) Prior Publication Data

US 2010/0268019 A1    Oct. 21, 2010

Related U.S. Application Data

(63) Continuation of application No. 11/367,758, filed on Mar. 3, 2006, now Pat. No. 7,727,142.

(51) Int. Cl.
| A61F 2/00 | (2006.01) |
| A61F 2/24 | (2006.01) |
| A61B 17/221 | (2006.01) |
| A61B 17/22 | (2006.01) |
| A61B 17/00 | (2006.01) |

(52) U.S. Cl.
CPC ....... *A61F 2/2481* (2013.01); *A61B 2017/2215* (2013.01); *A61B 2017/22035* (2013.01); *A61F 2002/2484* (2013.01); *A61B 2017/00243* (2013.01)
USPC ............................................. 600/37; 606/139

(58) Field of Classification Search
USPC .................. 600/37, 16–18; 606/138–150
See application file for complete search history.

(56) References Cited

U.S. PATENT DOCUMENTS

| 3,983,863 A | 10/1976 | Janke et al. |
| 4,048,990 A | 9/1977 | Goetz |

(Continued)

FOREIGN PATENT DOCUMENTS

| DE | 38311540 A1 | 6/1993 |
| EP | 0280564 | 8/1988 |

(Continued)

OTHER PUBLICATIONS

"Abstracts From the 68th Scientific Sessions, Anaheim Convention Center, Anaheim, California, Nov. 13-16, 1995", American Heart Association Supplement to Circulation, vol. 92, No. 8, Abstracts 1810-1813 (Oct. 15, 1995).

(Continued)

*Primary Examiner* — Catherine B Kuhlman
(74) *Attorney, Agent, or Firm* — Gordon Rees Scully Mansukhani LLP

(57) ABSTRACT

A device for delivery of a cardiac support device for treating cardiac disease of a heart includes a multistage deployment mechanism and an actuating mechanism for controlling the positions of the deployment mechanism. The deployment mechanism is operable to change between a retracted state and an extended state, and includes a plurality of independent stages, including, in one embodiment, a first stage including a guide structure for location adjacent a portion of the patient's heart when in the extended state. A second stage is movably coupled to the first stage, and is guided by the guide structure between the retracted and extended states. The second stage further releasably engages and supports the cardiac support device and positions the cardiac support device at the desired implantation location, guided by the guide structure of the stage. In some embodiments, the deployment mechanism may include additional stages. The actuating mechanism drives the deployment mechanism between the retracted and extended states, and independently controls the positions of the multiple stages of the deployment mechanism.

6 Claims, 6 Drawing Sheets

(56) References Cited

U.S. PATENT DOCUMENTS

| | | | |
|---|---|---|---|
| 4,403,604 A | 9/1983 | Wilkinson et al. | |
| 4,428,375 A | 1/1984 | Ellman | |
| 4,630,597 A | 12/1986 | Kantrowitz et al. | |
| 4,690,134 A | 9/1987 | Snyders | |
| 4,821,723 A | 4/1989 | Baker, Jr. et al. | |
| 4,834,707 A | 5/1989 | Evans | |
| 4,878,890 A | 11/1989 | Bilweis | |
| 4,936,857 A | 6/1990 | Kulik | |
| 4,957,477 A | 9/1990 | Lundback | |
| 4,973,300 A | 11/1990 | Wright | |
| 4,976,730 A | 12/1990 | Kwan-Gett | |
| 5,057,117 A | 10/1991 | Atweh | |
| 5,087,243 A | 2/1992 | Avitall | |
| 5,131,905 A | 7/1992 | Grooters | |
| 5,150,706 A | 9/1992 | Cox et al. | |
| 5,186,711 A | 2/1993 | Epstein | |
| 5,192,314 A | 3/1993 | Daskalakis | |
| 5,256,132 A | 10/1993 | Snyders | |
| 5,290,217 A | 3/1994 | Campos | |
| 5,356,432 A | 10/1994 | Rutkow et al. | |
| 5,366,460 A | 11/1994 | Eberbach | |
| 5,383,840 A | 1/1995 | Heilman et al. | |
| 5,385,156 A | 1/1995 | Oliva | |
| 5,405,360 A | 4/1995 | Tovey | |
| 5,429,584 A | 7/1995 | Chiu | |
| 5,507,779 A | 4/1996 | Altman | |
| 5,524,633 A | 6/1996 | Heaven et al. | |
| 5,603,337 A | 2/1997 | Jarvik | |
| 5,634,931 A | 6/1997 | Kugel | |
| 5,647,380 A | 7/1997 | Campbell et al. | |
| 5,702,343 A | 12/1997 | Alferness | |
| 5,713,954 A | 2/1998 | Rosenberg et al. | |
| 5,766,216 A | 6/1998 | Gangal et al. | |
| 5,800,528 A | 9/1998 | Lederman et al. | |
| 5,928,250 A | 7/1999 | Koike et al. | |
| 5,961,440 A | 10/1999 | Schweich, Jr. et al. | |
| 5,984,932 A * | 11/1999 | Yoon | 606/147 |
| 5,990,378 A | 11/1999 | Ellis | |
| 6,077,218 A | 6/2000 | Alferness | |
| 6,085,754 A | 7/2000 | Alferness et al. | |
| 6,123,662 A | 9/2000 | Alferness et al. | |
| 6,126,590 A | 10/2000 | Alferness | |
| 6,155,968 A | 12/2000 | Wilk | |
| 6,155,972 A | 12/2000 | Nauertz et al. | |
| 6,165,121 A | 12/2000 | Alferness | |
| 6,165,122 A | 12/2000 | Alferness | |
| 6,179,791 B1 | 1/2001 | Krueger | |
| 6,193,648 B1 | 2/2001 | Krueger | |
| 6,241,654 B1 | 6/2001 | Alferness | |
| 6,293,906 B1 * | 9/2001 | Vanden Hoek et al. | 600/37 |
| 6,375,608 B1 | 4/2002 | Alferness | |
| 6,416,459 B1 | 7/2002 | Haindl | |
| 6,425,856 B1 | 7/2002 | Shapland et al. | |
| 6,482,146 B1 | 11/2002 | Alferness et al. | |
| 6,537,203 B1 | 3/2003 | Alferness et al. | |
| 6,544,168 B2 | 4/2003 | Alferness | |
| 6,569,082 B1 | 5/2003 | Chin | |
| 6,572,533 B1 | 6/2003 | Shapland et al. | |
| 6,579,226 B2 | 6/2003 | Vanden Hoek et al. | |
| 6,682,476 B2 | 1/2004 | Alferness | |
| 6,689,048 B2 | 2/2004 | Vanden Hoek et al. | |
| 6,702,732 B1 | 3/2004 | Lau et al. | |
| 6,723,041 B2 * | 4/2004 | Lau et al. | 600/37 |
| 6,755,779 B2 | 6/2004 | Vanden Hoek et al. | |
| 6,881,185 B2 | 4/2005 | Vanden Hoek et al. | |
| 6,902,524 B2 | 6/2005 | Alferness et al. | |
| 6,908,426 B2 | 6/2005 | Shapland et al. | |
| 6,951,534 B2 | 10/2005 | Girard et al. | |
| 7,621,866 B2 | 11/2009 | Dietz et al. | |
| 7,727,142 B2 * | 6/2010 | Hjelle et al. | 600/37 |
| 2004/0138521 A1 * | 7/2004 | Grabek et al. | 600/37 |
| 2005/0059854 A1 | 3/2005 | Hoek et al. | |
| 2005/0059855 A1 | 3/2005 | Lau et al. | |
| 2005/0090707 A1 | 4/2005 | Lau et al. | |
| 2005/0171589 A1 | 8/2005 | Lau et al. | |
| 2005/0256368 A1 | 11/2005 | Kienk | |
| 2005/0288715 A1 | 12/2005 | Lau et al. | |
| 2006/0009831 A1 | 1/2006 | Lau et al. | |

FOREIGN PATENT DOCUMENTS

| | | |
|---|---|---|
| GB | 2209678 | 5/1989 |
| JP | 01-145066 | 6/1989 |
| JP | 02-0271829 | 11/1990 |
| WO | WO 96/16601 | 6/1996 |
| WO | WO 98/29041 | 7/1998 |
| WO | WO 98/58598 | 12/1998 |
| WO | WO 99/44534 | 9/1999 |
| WO | WO 00/01306 | 1/2000 |
| WO | WO 01/67985 | 9/2001 |

OTHER PUBLICATIONS

Capomolla et al., "Dobutamine and nitroprusside infusion in patients with severe congestive heart failure: Hemodynamic improvement by discordant effects on mitral regurgitation, left atrial function, and ventricular function", American Heart Journal, vol. 134, No. 6, pp. 1089-1098 (Dec. 1997).

Capouya et al., "Girdling Effect of Nonstimulated Cardiomyoplasty on Left Ventricular Function", The Society of Thoracic Surgeons, vol. 56, pp. 867-871 (1993).

Cohn, "The Management of Chronic Heart Failure", The New England Journal of Medicine, vol. 335, No. 7, pp. 490-498 (Aug. 15, 1996).

Colleta et al., "Prognostic value of left ventricular volume response during dobutamine stress echocardiography", European Heart Journal, vol. 18, pp. 1599-1605 (Oct. 1997).

Guasp, "Una protasis contentiva para el tratamiento de la miocardiopatia dilatada" Revista Espanola de Cardiologia, vol. 51, No,7, pp. 521-528 (Jul. 1995).

Kass et al,, "Reverse Remodeling From Cardiomyoplasty in Human Heart Failure", Circulation, vol. 91, No. 9, pp. 2314-2318 (May 1, 1995).

Levin et al., "Reversal of Chronic Ventricular Dilation in Patients With End=Stage Cardiomyopathy by Prolonged Mechanical Unload", Circulation, vol. 91, No. 11, pp. 2717-2720 (Jun. 1, 1995).

Oh et al., "The Effects of Prosthetic Cardiac Binding and Adynamic Cardiomyoplasty in A Model of Dilated Cardiomhyopathy", The Journal of Thoracic and Cardiovascular Surgery, vol. 116, No. 1, pp. 148-153 (Jul. 1998).

Paling, "Two-Bar Fabrics (Part-Set Threading)", Warp Knitting Technology; Columbine Press (Publishers) Ltd., Buxton, Great Britain, p. 111 (1970).

Vaynblat et al., "Cardiac Binding in Experimental Heart Failure", Ann Thorac Surg. vol. 64 (1997).

* cited by examiner

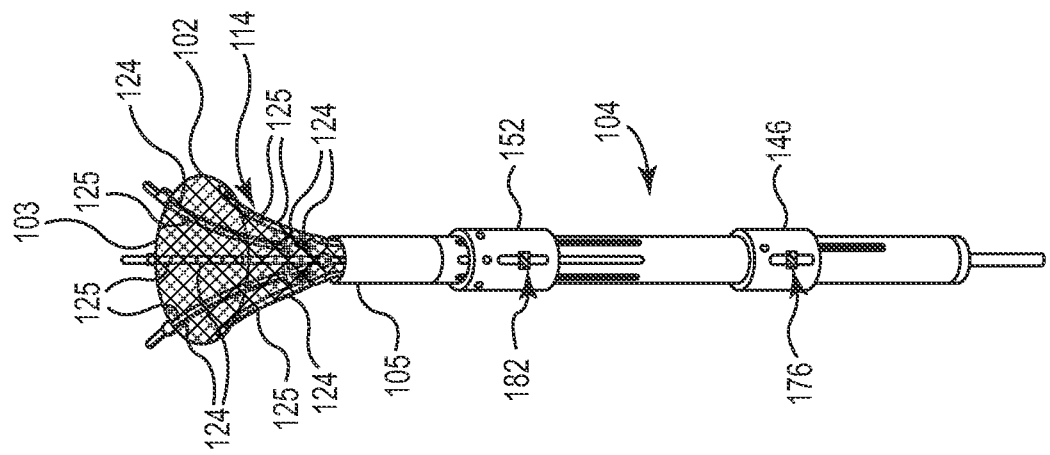
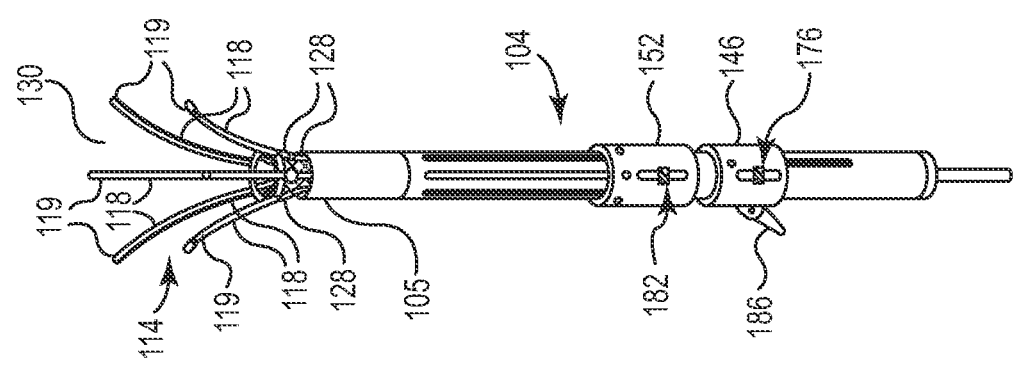
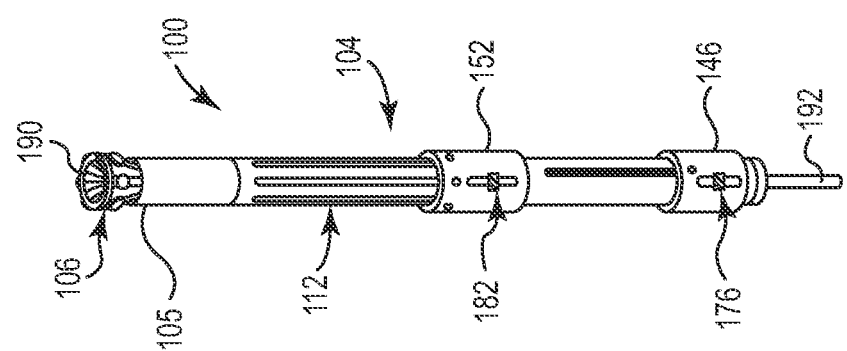

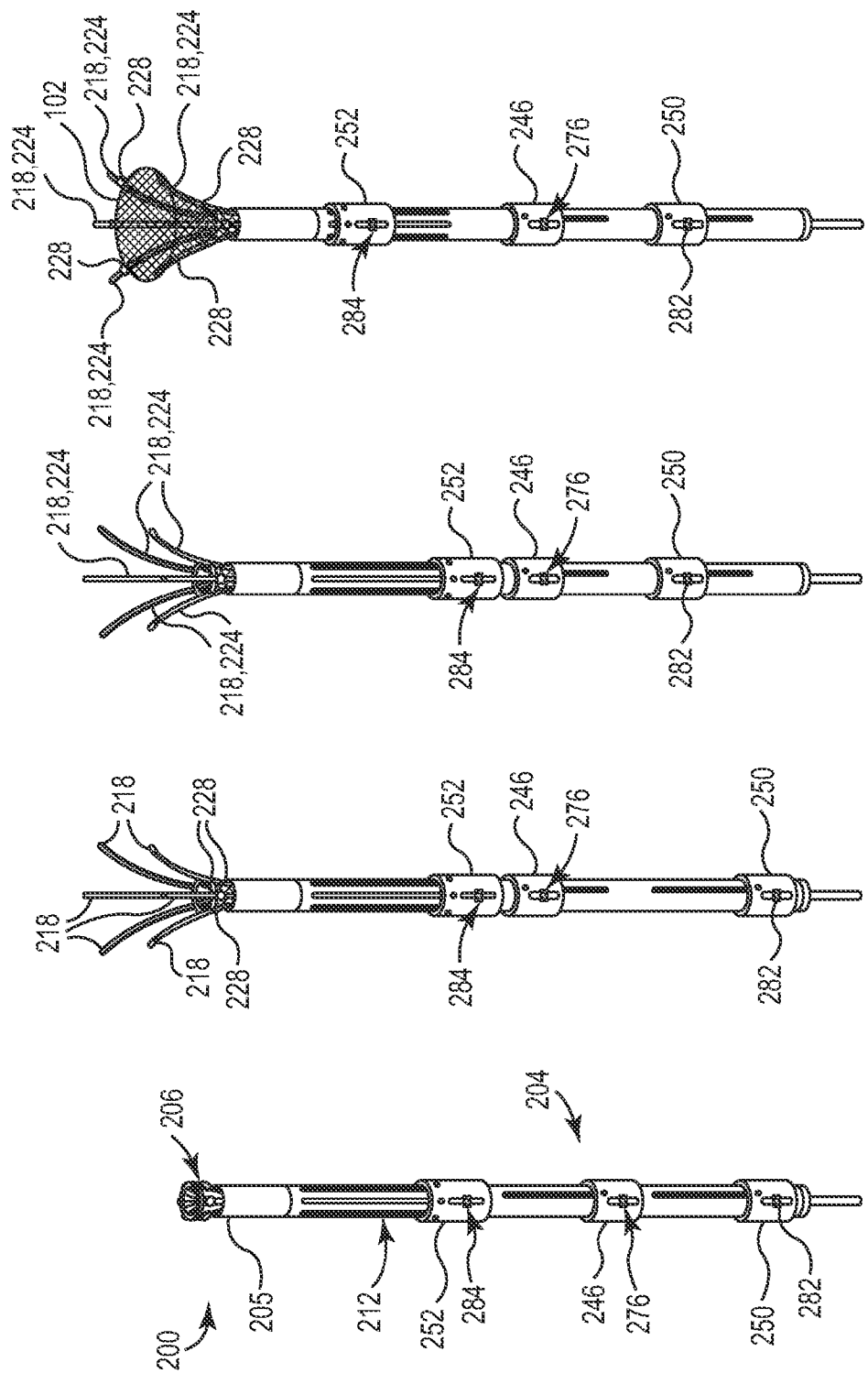

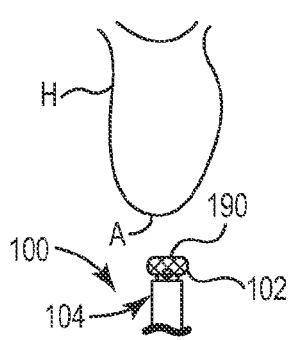 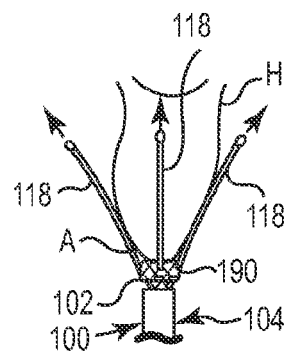 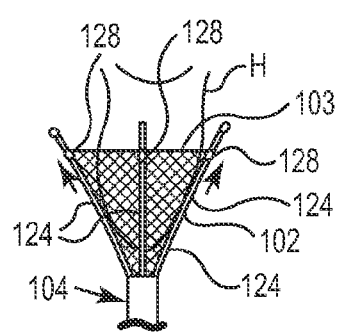
Fig. 15      Fig. 16      Fig. 17
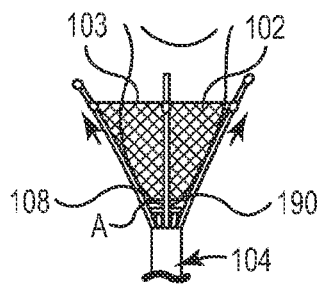
Fig. 18
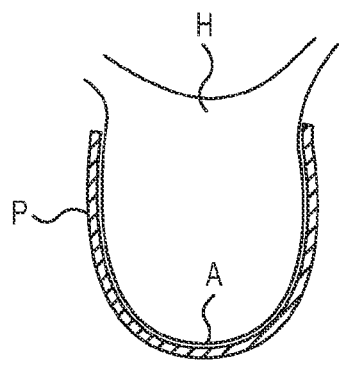 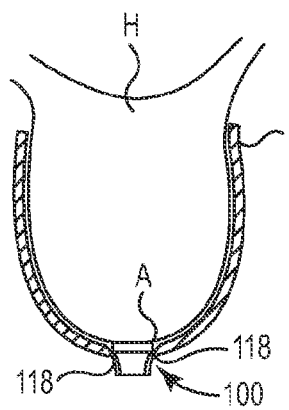 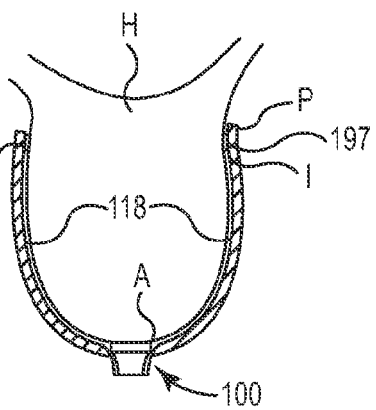
Fig. 19      Fig. 20      Fig. 21

CARDIAC SUPPORT DEVICE DELIVERY TOOL WITH INDEPENDENTLY MOVABLE ARMS

CROSS-REFERENCE TO RELATED APPLICATION

This application is a continuation of U.S. patent application Ser. No. 11/367,758, filed Mar. 3, 2006, now issued as U.S. Pat. No. 7,727,142, entitled DELIVERY TOOL FOR CARDIAC SUPPORT DEVICE, which application is incorporated herein by reference in its entirety and for all purposes.

FIELD OF THE INVENTION

The present invention pertains to a method and apparatus for treating congestive heart disease and related valvular dysfunction. More particularly, the present invention is directed to an apparatus and method for delivery of a cardiac support device.

BACKGROUND OF THE INVENTION

Various cardiac support devices for treating congestive heart disease are known. One exemplary type of cardiac support device includes a cardiac jacket for reducing tension in the heart wall by constraining or resisting expansion of the heart. Devices and methods for delivering cardiac support devices using minimally invasive surgical procedures are also known. Such cardiac support devices and/or cardiac support device delivery devices are described, for example, in U.S. Pat. No. 5,702,343; U.S. Pat. No. 6,155,972; U.S. Pat. No. 6,193,648; U.S. Pat. No. 6,293,906; U.S. Pat. No. 6,482,146; U.S. Pat. No. 6,682,476; U.S. Pat. No. 6,902,524; U.S. Pat. No. 6,425,856; U.S. Pat. No. 6,908,426; U.S. Pat. No. 6,572,533; and U.S. Pat. No. 6,951,534, all of which are assigned to Acorn Cardiovascular, Inc. and are incorporated herein by reference.

Other embodiments of cardiac support devices and/or cardiac support device delivery devices are disclosed in U.S. Pat. No. 6,702,732; U.S. Pat. No. 6,723,041; U.S. patent application publication no. US 2006/0009831 A1 published Jan. 12, 2006; U.S. patent application publication no. US 2005/0288715 published Dec. 29, 2005; U.S. patent application publication no. US 2005/0256368 A1 published Nov. 17, 2005; U.S. patent application publication no. US 2005/0171589 published Aug. 4, 2005; U.S. patent application publication no. US 2005/0090707 A1 published Apr. 28, 2005; and U.S. patent application publication no. US 2005/0059855 A1 published Mar. 17, 2005, all of which are incorporated herein by reference.

There remains, however, a continuing need for improved delivery devices for cardiac support devices. In particular, there is a need for a delivery device for accurately deploying a cardiac support device at a desired position on the heart and which can be used for minimally invasive implantation procedures.

SUMMARY OF THE INVENTION

The present invention is a device and method for delivery of a cardiac support device for treating congestive heart disease. In one embodiment, the delivery device includes a multistage deployment mechanism including a first stage movable between a first state and a second state adjacent a side of a heart, and a second stage movable with respect to the first stage between first and second states for releasably supporting the cardiac support device and positioning the cardiac support device on the heart. An actuating mechanism is coupled to the deployment mechanism for actuating the first and second stages between the first and second states.

BRIEF DESCRIPTION OF THE DRAWINGS

FIG. 1 is a perspective view of a delivery device according to one embodiment of the present invention shown with a multistage deployment mechanism in a retracted state.

FIG. 2 is the view of the delivery device of FIG. 1 showing a first stage of the multistage deployment mechanism moved to an extended state and further showing a cardiac support device engaged with a second stage of the deployment mechanism in a retracted state.

FIG. 3 is a perspective view of the delivery device of FIG. 1 shown in a substantially fully extended state and supporting a cardiac support device for deployment over a patient's heart.

FIGS. 10-13 are perspective views of a delivery device according to another embodiment of the present invention utilizing a three stage deployment mechanism.

FIGS. 15-17 are schematic views of the distal end of the delivery device of FIGS. 1-3 in use in deploying a cardiac support device over a patient's heart.

FIG. 18 is a schematic view of the distal end of a delivery device according to one embodiment showing an open apex end cardiac support device in a deployed position over a patient's heart.

FIGS. 19-21 are schematic views of the distal end of a delivery device according to various embodiments of the present invention shown deploying the primary members of the deployment mechanism through an incision in the pericardium of the patient's heart.

DETAILED DESCRIPTION OF THE PREFERRED EMBODIMENTS

Figure 4:
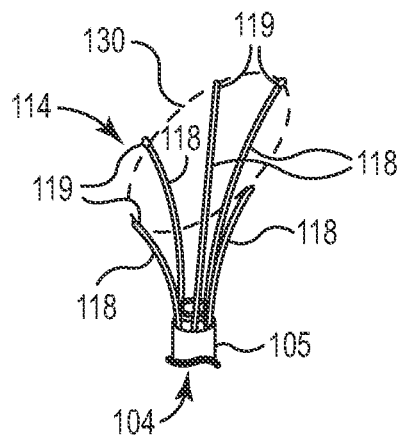
FIG. 4 is a perspective view of a distal end of the delivery device of FIGS. 1-3 showing the primary members of the multistage deployment mechanism in an extended state.

FIGS. 1-3 are perspective views of a delivery device 100 according to one embodiment of the present invention shown supporting a cardiac support device 102 for deployment over a patient's heart. The cardiac support device 102 includes a base end 103 and may be any type of cardiac support device, including, without limitation, any of the devices disclosed in any of the patents and patent publications referenced and incorporated above in the Background of the Invention.

As shown in FIGS. 1-3, the delivery device 100 includes a body 104 having a distal end 105, a multistage deployment mechanism 106, and an actuating mechanism 112 on the body 104 operatively coupled to the deployment mechanism 106. The multistage deployment mechanism 106 is operable to change between a first retracted or closed state, as shown in FIG. 1, and a second extended or open state, as shown in FIGS. 2-3, and is adapted to releasably support the cardiac support device 102 and to accurately position the cardiac support device 102 at a desired implantation position on the patient's heart. The actuating mechanism 112 drives the deployment mechanism 106 between the retracted and extended states for positioning the cardiac support device 102 on the heart.

In the embodiment illustrated in FIGS. 1-3, the multistage deployment mechanism 106 includes a first stage which in the extended state forms a guide structure 114 for guiding and/or positioning a second or cardiac support device positioning stage for positioning the cardiac support device on the heart. In the illustrated embodiment, the first stage includes a plurality of elongated primary members 118, and the second stage includes a plurality of elongated secondary members 124. Each of the primary and secondary members 118, 124 includes a distal end 119, 125, respectively. As illustrated, in the extended state, the primary members 118 form the guide structure 114 for supporting and/or guiding the second stage. The guide structure 114 can be located adjacent at least a portion of the heart. In the illustrated embodiment of FIGS. 2-3, the distal ends 119 of the primary members 118 form a generally circular open array 130. Each of the secondary members 124 is slidably (i.e., movably) coupled to a respective primary member 118, and at least some of the secondary members 124 are adapted to releasably engage and support the cardiac support device 102 via support or engagement structures 128.

The secondary members 124 are guided and supported by the primary members 118 to position the cardiac support device 102 at the desired location and orientation on the patient's heart. The primary members 118 can be used initially to accurately locate the optimal attachment location and orientation for the cardiac support device 102, and the secondary members 124 can then be used to releasably support the cardiac support device 102 with the base end 103 in an open position such that the cardiac support device 102 can be slid over the heart guided by the primary members 118. This multistage configuration is particularly advantageous for accurately positioning the cardiac support device 102 on the heart in minimally invasive surgical procedures in which the physician lacks direct visual access to the heart.

As illustrated in FIGS. 1-3, the actuating mechanism 112 includes a first stage actuating mechanism which, in this embodiment, is a first sliding handle 146 on the body 104, and a second stage actuating mechanism which in the illustrated embodiment is a second sliding handle 152 on the body 104. The first sliding 146 handle is coupled to the primary members 118, and the second sliding handle 152 is coupled to the secondary members 124. The sliding handles 146 and 152 are actuated to drive the primary and secondary members 118 and 124, respectively, between the extended and retracted states. As shown in FIG. 1, in a first or retracted state of the first sliding handle 146, the primary members 118 are in the retracted state and are contained substantially within the interior of the tubular body 104. As shown in FIG. 2, driving the first sliding 146 handle distally from its retracted state to a second or unretracted state drives the primary members 118 to the extended state in which the primary members 118 are extended distally from the distal end 105 of the body 104 and form the guide structure 114.

As shown in FIGS. 1 and 2, in a first or retracted state of the second sliding handle 152, the secondary members 124 are in the retracted state and are contained substantially within the interior of the tubular body 104. As shown in FIG. 3, driving the second sliding handle 152 distally from the retracted state to a second or unretracted state drives the secondary members 124 out of the body 104 to slide along the primary members 118 toward the distal ends 119 of the primary members 118. In some embodiments (not shown), the deployment mechanism 106 can rotate independently of the body 104 about a longitudinal axis of the body 104.

The primary members 118 are preshaped and resilient such that the distal ends 119 extend radially outwardly with respect to the longitudinal axis of the body 104 when in the extended state. Thus, with the primary members 118 in the extended state as shown in FIG. 2, the secondary members 124 can releasably support the cardiac support device 102 with the base end 103 in an open position and can advance the cardiac support device 102 over the heart guided by the primary members 118.

As further shown in FIGS. 1-3, the actuating mechanism 112 includes individual actuating mechanisms 176 and 182, each operatively coupled to an individual primary member 118 and an individual secondary member 124, respectively. The individual actuating mechanisms 176, 182 operate to independently move the respective primary and secondary members 118 and 124. In the embodiment illustrated in FIGS. 1-3, the individual actuating mechanisms 176 and 182 drive individual primary and secondary members 118, 124 over relatively limited ranges. This configuration is advantageous in permitting relatively fine adjustments to the position of the respective primary and secondary members 118 and 124 to accommodate particular heart anatomies. In other embodiments (not shown), one or more of the primary members 118 and/or secondary members 124 may be individually movable over a wider range of motion than is shown in FIGS. 1-3. Although FIGS. 1-3 illustrate a delivery device 100 including one each of the individual actuating mechanisms 176 and 182, those skilled in the art will appreciate that additional or all of the primary and secondary members 118, 124 may be individually movable via additional individual actuating mechanisms. Furthermore, in other embodiments, the individual actuating mechanisms 176 and/or 182 are omitted.

The actuating mechanism 112, in the illustrated embodiment, includes a tab 186 operatively connected to a cam or detent mechanism (not shown) which operates to lock the sliding handle 146, and in turn, the primary members 118, in a desired position. Other structures (e.g., set screws) can also be used to provide the locking function. Additionally, it will be appreciated that similar structures may be provided for locking the secondary members 124. Alternatively, the locking structures may be omitted.

Additionally, the actuating mechanism 112 may include the capability to independently lock axial and rotational movement of the deployment mechanism 106. That is, the actuating mechanism 112 may be configured such that the axial position of the deployment mechanism 106 may be locked, but the deployment mechanism 106 may still be rotatable about the longitudinal axis of the body 104. Alternatively, such rotation of the deployment mechanism 106 may be locked, while the deployment mechanism 106 may still be permitted to move axially.

As further shown in FIGS. 1-3, the delivery device 100 includes an epicardial stabilization device 190 for atraumatically grasping or engaging the epicardial tissue to stabilize the heart during implantation of the cardiac support device 102. In the illustrated embodiment, the epicardial stabilization device 190 includes a suction cup connected to a suction tube 192, which may in turn be connected to a source of suction. In other embodiments not shown, the epicardial stabilization device 190 may include other structures or means (e.g., adhesive) for atraumatically grasping the heart tissue or, alternatively, may be omitted.

Figure 5:
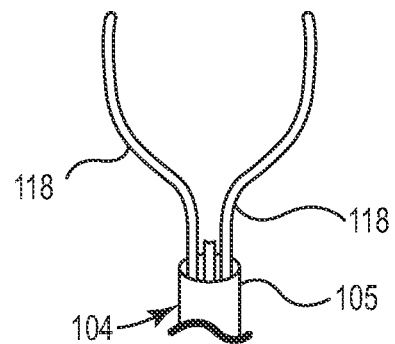
FIG. 5 is a perspective view of a distal end of the delivery device of FIGS. 1-3 showing an alternative embodiment of the primary members of the multistage deployment mechanism in an extended state.

FIGS. 4 and 5 depict alternative embodiments of the primary members 118 of the deployment mechanism 106 extended distally from the distal end 105 of the body 104. In the embodiment illustrated in FIG. 4, the primary members 118 are configured such that in the extended state they form the guide structure 114 in which the open array 130 is generally elliptical (as indicated by the dashed line in FIG. 4), having its plane at an angle to the longitudinal axis of body 104 to generally match the orientation of the atrio-ventricular (A-V) groove of a typical heart. In other embodiments (not shown), the primary members 118 may be configured to open to an irregularly shaped array adapted to more closely match the anatomical shape of the A-V groove of the patient's heart. FIG. 5 illustrates exemplary primary members 118 according to an alternative embodiment, in which the primary members 118 are pre-shaped to extend initially radially away from the longitudinal axis of the body 104, then straighten or extend radially inwardly near their distal ends 119 (only two primary members 118 are shown extended in FIG. 5, although it will be appreciated that fewer or more than two such primary members 118 may be present). The primary members 118 according to such embodiments are configured to more closely conform to the shape of the heart. In both of the foregoing embodiments, the primary members 118 are resilient such that they can be retracted within the body 104 when in the retracted state.

Figure 6:
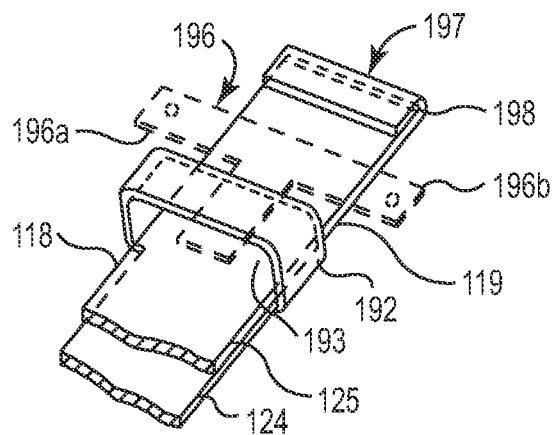
FIG. 6 is a view of the distal ends of primary and secondary members of the deployment mechanism of FIGS. 1-3.

FIG. 6 illustrates the distal ends 119, 125 of a pair of the primary and secondary members 118, 124, according to one embodiment of the present invention. As shown in FIG. 6, the secondary member 124 includes a clip 192 which surrounds the primary member 118 and slidably couples the secondary member 124 to the primary member 118. In some embodiments (not shown), the secondary member 124 may include a plurality of clips 192 spaced at multiple locations along the secondary member 124 to prevent buckling of the secondary member 124 relative to the primary member 118.

FIG. 6 also shows one exemplary embodiment for releasably engaging and supporting the cardiac support device 102. In the illustrated embodiment, the clip 192 also operates to releasably engage a portion of the cardiac support device 102. As shown, the clip 192 is shaped to form a channel 193 which receives a portion of a tab 196 (shown in phantom lines in FIG. 6) which in turn can be attached to the cardiac support device 102. As is apparent in FIG. 6, upon the lateral arms 196*a*, 196*b* of the tab 196 contacting the clip 192, the tab 196 will move distally along with the secondary member 124, while proximal movement of the secondary member 124 will disengage the tab 196 to release the cardiac support device 102 from the clip 192. Alternatively, or additionally, a push rod or similar structure may be used to force the tab 196 out of the channel 193 (not shown).

As further shown in FIG. 6, the primary member 118 includes an atraumatic distal tip 197 formed by folding over a portion of the distal end of the primary member 118. Additionally or alternatively, the tip 197 may be made from a relatively soft material to avoid tissue damage. The tip 197 may also include a radiopaque marker, which in the embodiment shown in FIG. 6, is a pin 198 made of any material (such as metal) which is readily apparent under fluoroscopy. In another embodiment, the tip 198 may itself be made radiopaque. In some embodiments, the tip 198 also provides a stop for the clip 192 of the secondary member 124.

Figure 7:
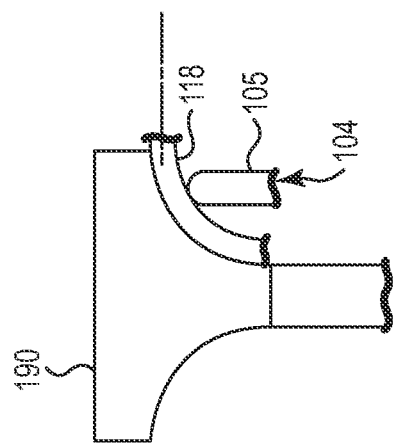
FIGS. 7-9 show alternative arrangements for directing the positioning of a primary member of the multistage deployment mechanism.
Figure 8:
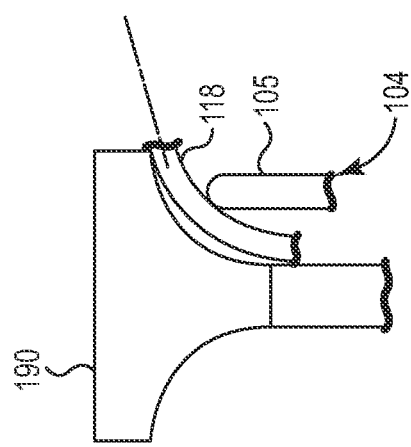
Figure 9:
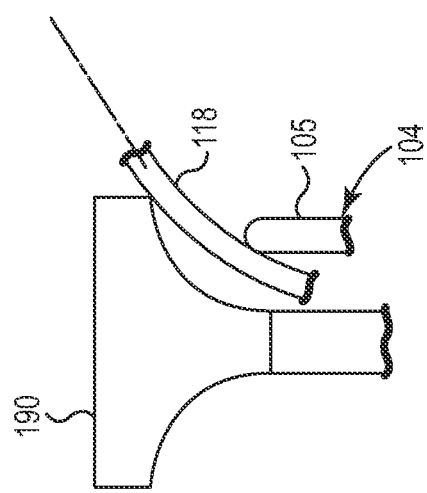

FIGS. 7-9 illustrate how positioning of the body 104 relative to the epicardial stabilization device 190 can influence the angle of deployment and configuration of the primary members 118 with respect to the distal end 105 of the body 104. As shown in FIGS. 7-9, as the body 104 is moved relatively closer in proximity to the epicardial stabilization device 190, the angle of deployment of the primary members 118 increases, until, as shown in FIG. 9, a near perpendicular angle of deployment may be provided. Thus, the positioning of the epicardial stabilization device 190 relative to the body 104 can be adjusted to permit the surgeon to control the angle at which the primary members 118 are deployed from the distal end 105 of the body 104.

In some embodiments, the flexibilities of the primary and secondary members 118, 124 may be defined so as to enhance the operational capabilities of the delivery device 100. For example, in some embodiments, the primary members 118 may advantageously be made more or less flexible than the secondary members 124. In particular, the primary members 118 can be configured to have relatively high flexibility to assist in navigating the primary members 118 around the epicardial surface without causing trauma to the heart tissue. The secondary members 124 can be made relatively rigid so as to stiffen the guide structure 114 for positioning the cardiac support device 102 on the heart. In other embodiments, flexibility among the plurality of primary members 118 varies.

In still other embodiments, one or more of the primary members 118 may have varying flexibility along their lengths. For example, in some circumstances, it will be advantageous to configure the primary members 118 such that their flexibilities increase in the distal direction to facilitate ease of deployment. Such variation in flexibility can be accomplished, for example, by decreasing the widths and/or thicknesses of the individual primary members 118 along their lengths. Alternative or additional techniques for varying the flexibilities of the primary and secondary members 118, 124, will be apparent to those skilled in the art.

The actuating mechanism 112 may be made from any materials typically used in devices for delivery of implantable medical devices. Similarly, the deployment mechanism 106 may be made from any materials having suitable rigidity and biocompatibility properties. Exemplary materials for the deployment mechanism 106 include, without limitation, metals (such as stainless steel), shape memory alloys (such as Nitinol), and polymers (such as polyeurethane and PEEK™).

FIGS. 10-13 illustrate a delivery device 200 according to another embodiment of the present invention. As shown in FIGS. 10-13, the delivery device 200 includes a body 204 having a distal end 205, a three stage deployment mechanism 206, and an actuating mechanism 212 on the body 204 and coupled to the deployment mechanism 206. The deployment mechanism 206 includes three sets of elongated members 218, 224, and 228. The members 218 and 228 are similar in design and function to the primary and secondary members 118, 124 of the delivery device 100 described above. That is, the elongated members 218 can be extended from the body 204 forming a guide structure for guiding the members 228, which can releasably support the cardiac support device 102 for positioning on the heart as described above. The members 224 are deployed to stabilize and stiffen the guide structure formed by the members 218 prior to positioning the cardiac support device 102 on the heart using the members 228. In one embodiment, each of the members 224 and 228 are slidably coupled to a respective member 218. In other embodiments, the members 228 are slidably coupled to respective members 224, which in turn are slidably coupled to respective members 218. Coupling of the respective members to one another can be accomplished as described above for the delivery device 100, or by other structures as described below.

The actuating mechanism 212 includes sliding handles 246, 250, and 252 connected to the members 218, 224, and 228, respectively. The sliding handles 246, 250 and 252 are operable to drive the members 218, 224 and 228 between their retracted and extended states. As shown, the actuating mechanism 212 further includes individual actuating mechanisms 276, 282, and 284 for individually actuating one of the members 218, 224, or 228, respectively. In other embodiments (not shown), additional or all of the members 218, 224, and 228 may be individually movable by additional individual actuating mechanisms. Alternatively, the individual actuating mechanisms may be omitted.

In operation, the members 218 are advanced distally to the desired position with respect to the heart, thereby forming the guide structure for guiding the members 228 for positioning the cardiac support device 102 on the heart. In some circumstances, it is desirable for the members 218 to be relatively flexible in order to navigate the pericardial space (i.e., due to interference by, for example, lesions or fibrotic tissue which otherwise impede distal movement of the members 218). The members 224 can then be advanced distally along the members 218 to stiffen and stabilize the support structure prior to deployment of the cardiac support device 102 releasably supported by the members 228.

Figure 14:
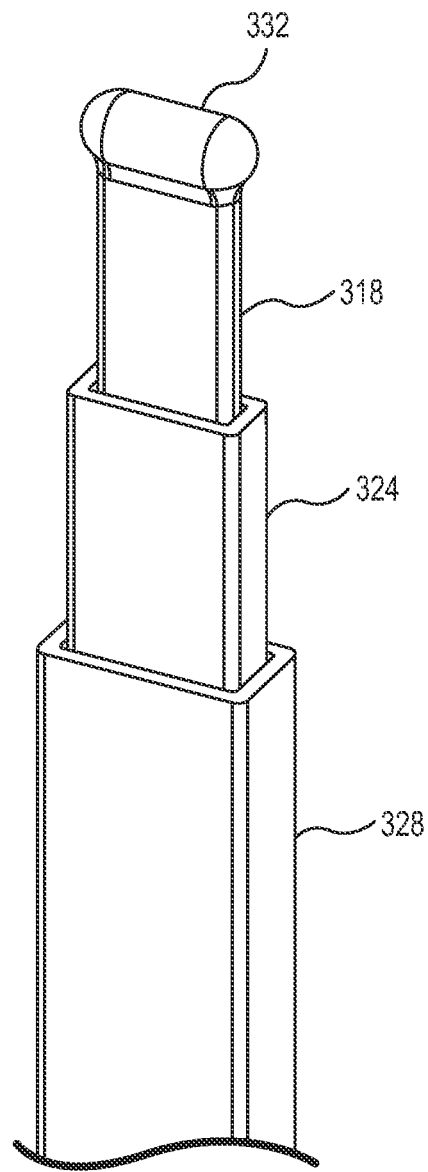
FIG. 14 is a perspective schematic view of a primary, secondary and tertiary member of a multistage deployment mechanism arranged according to another embodiment of the present invention.

FIG. 14 illustrates an assembly of members 318, 324, and 328 for a three-stage deployment mechanism according to another embodiment of the present invention. As shown in FIG. 14, the members 324, 328 are generally tubular and are arranged substantially coaxially with the member 324 disposed within the member 328. The member 318 is disposed within the member 324 and includes a rounded, atraumatic distal tip 332. The distal tip 332 may also be made radiopaque to assist the physician in proper positioning of the members 318 with respect to the heart. The members 318 and 328 function in much the same manner as the primary and secondary members 118, 124 of the delivery device 100 described above. The member 324 operates to stiffen the member 318 after its deployment. Thus, like the members 218 described above, the member 318 may be made relatively flexible to promote ease of deployment, although this is not a requirement. Each of the members 318, 324, and 328 can be driven independently by an actuating mechanism (not shown). It will be appreciated that the substantially coaxial member structure of FIG. 14 can be used for delivery devices having deployment mechanisms with two stages or more than three stages.

The delivery devices according to the various embodiments of the present invention are not limited in terms of the number of stages that may be present in the multistage deployment mechanisms. To the contrary, delivery devices incorporating deployment mechanisms having more than three stages are contemplated within the scope of the present invention. Similarly, in embodiments including one or more elongated members in one or more of the individual stages, the number of elongated members in any individual stage is not limited.

The actuating mechanism of the delivery device can include any structure adapted for independently controlling the positions of the stages of the multistage deployment mechanism. For example, in lieu of the sliding handles described above, the deployment mechanism may have rotating handles that can rotate in a threaded track in the body of the actuating mechanism, with such rotation translated by a linkage into axial and/or rotational motion of the deployment mechanism. Alternatively, the actuating mechanism may include handles that both rotate and slide axially along the body of the actuating mechanism. Still alternatively, pneumatic, hydraulic, or electric systems (e.g., servo motors) may be used to drive the stages of the deployment mechanism between the retracted and extended states.

Additionally, the body of the actuating mechanism need not have a tubular structure as shown and described in the foregoing embodiments. Rather, in some embodiments not shown, the body is substantially solid, or includes both solid and tubular segments. Additionally, the body of the actuating mechanism can have a non-circular cross-sectional shape. In some embodiments, the body is made substantially rigid along substantially its entire length, or alternatively, is relatively flexible. In yet other embodiments, the body includes two or more substantially rigid portions pivotally connected such that the distal end of the delivery device can be set at an angle relative to the proximal end of the delivery device.

Furthermore, in some embodiments, the multistage deployment mechanism is not be retractable within the body portion. For example, in some embodiments not shown (e.g., those utilizing a non-tubular actuating mechanism body), the primary and/or secondary members can travel within guides, channels, or similar structures disposed along the outside of the body.

Additionally, while the Figures show the cardiac support device 102 disposed on the inside of the secondary members 124 of the deployment mechanism 106 and the members 228 in the three stage embodiment of FIGS. 10-13 (i.e., the cardiac support device positioning stage), in other embodiments, the cardiac support device 102 is disposed on the outside of these members. Similarly, although the Figures illustrate the secondary members 124 disposed on the inside of the primary members 118, in other embodiments not shown, the second stage is disposed on the outside of the first stage. That is, there is no requirement that the cardiac support device positioning stage occupy any particular radial location in the multistage deployment mechanism.

Any structures and methods for releasably engaging and supporting the cardiac support device 102 can be used within the scope of the present invention. For example, in addition to the arrangement shown in FIG. 6 and described above, the deployment mechanism can releasably engage and support the cardiac support device 102 by engaging loops or atraumatic hooks attached to or incorporated into the cardiac support device 102. Alternatively, the cardiac support device 102 can be releasably engaged using adhesives, magnets, or removable sutures or stitches.

The members of the respective stages can be movably or slidably coupled to each other by any structure known in the art. For example, in addition to the clip arrangement and telescoping configurations described above, in other embodiments not shown, a channel can be formed in the primary member (e.g., by folding over the sides of the primary member), and the secondary member can be slidably retained therein. Alternatively, the primary or secondary member can include a slot, and the other of the secondary or primary member can include a key sized to be slidably captured within the slot.

In still other embodiments not shown, the independent stages (e.g., the first and second stages of the deployment mechanism 106 described above) are not coupled. For example, the first stage can perform a positioning function to identify the optimal implantation position and orientation of cardiac support device. In such embodiments the cardiac support device positioning stage (e.g., the second stage of the delivery device 100) can navigate the epicardial surface and position the cardiac support device on the heart using the extended first stage as a navigation aid and guide even where the first and second stages are not mechanically coupled.

Moreover, the multistage deployment mechanism is not limited to the illustrated structures utilizing elongated members to form the respective stages. For example, the independent stages can include elastic rings in lieu of, or in addition to, the elongated primary and secondary members, which rings are collapsed when in the retracted state, and which self-expand to at least partially surround the patient's heart upon being extended distally from the body driven by the actuating mechanism.

FIGS. 15-17 illustrate a cardiac support device 102 being positioned over the patient's heart H using, in this example, the delivery device 100 according to one embodiment of the present invention. As will be appreciated by those skilled in the art, other delivery device embodiments according to the present invention, such as the embodiment shown in FIGS. 10-13, may also be used. In this example, the delivery device 100 includes the epicardial stabilization device 190, which may be a suction cup. As discussed above, however, the epicardial stabilization device 190 may be omitted. For example, the body 104 may terminate at a blunt distal end which can be simply placed against the heart surface and held in place by the surgeon manipulating the body 104.

As illustrated schematically in FIGS. 15 and 16, the distal end of the delivery device 100 is advanced toward the apex A of the heart H and the epicardial stabilization device 190 is placed against the apex A to stabilize the heart H. If the epicardial stabilization device 190 includes a suction cup, suction can be applied to retain the epicardial stabilization device 190 against the apex A of the heart.

In FIGS. 15-17, the cardiac support device 102 is a closed apex end cardiac support device which is folded over the epicardial stabilization device 190, and the remainder of the device 102 is collapsed within the body 104 with the base end 103 of the cardiac support device 102 engaged at the engagement structures 128 of the secondary members 124.

The first handle 146 is moved distally to deploy the primary members 118 as shown in FIG. 16. Subsequently, the secondary members 124 can be deployed by moving the second handle 152 distally to position the cardiac support device 102 with its base end 103 open and surrounding the heart as shown in FIG. 17. The base end 103 of the cardiac support device 102 is then disengaged from the secondary members 124 and the primary members 118 and secondary members 124 can be retracted into the body 104, which can be then removed from the patient.

In one embodiment, all of the primary members 118 may be simultaneously deployed, and all of the secondary members 124 may further be simultaneously deployed, by movement of the handles 146, 152, respectively. However, as discussed above, the individual primary and/or secondary members 118, 124 could be individually controlled by individual controllers.

FIG. 18 shows an alternative embodiment as an open apex end 108 cardiac support device 102'. With such a device, no portion of the cardiac support device 102' need cover the epicardial stabilization device 190 (when present).

When desired, the anatomy of the heart H can be used to retain the primary members 118 in close proximity to the surface of the heart. For example, FIG. 19 illustrates a pericardium P which is a sac surrounding the heart. In practice, the surgeon can make an incision through the pericardium P near the apex A of the heart H. The distal end of the delivery device 100 can then be advanced through the incision into contact with the apex A of the heart H as illustrated in FIG. 20. In circumstances where the apex A of a diseased heart may be difficult to identify because the heart H has deformed into a more spherical geometry, the general location of the apex A of the heart H can be identified. The primary members 118 can be moved, either collectively or individually, until the distal ends of the primary members 118 are placed around the general vicinity of the A-V groove of the heart H as illustrated in FIG. 21. Positioning of the primary members 118 in a desired location near the A-V groove can be inspected through fluoroscopy, aided, for example, by the radiopaque distal tips 197 of the primary members 118. Throughout this placement, the pericardium P maintains the primary members 118 in close proximity to the surface of the heart H as illustrated in FIG. 21. Once the primary members 118 are positioned in the desired location, the secondary members are moved to the extended state delivering the cardiac support device in a desired positioning around the heart as described above. The cardiac support device is then disengaged and the guide arms and attachment arms are retracted into the tool which is removed from the patient.

Various modifications and additions may be made to the exemplary structures and steps discussed without departing from the scope of the present invention. Various combinations, permutations, and rearrangements of those structures and steps may similarly be made without departing from the scope of the present invention. Accordingly, the scope of the present invention is intended to embrace all such alternatives, modifications, permutations and variations as fall within the scope of the claims, together with all equivalents thereof.

What is claimed is:

1. A cardiac support device (CSD) delivery apparatus, comprising:
    a body;
    a deployment mechanism including:
        an array of primary elongate members configured to select a location on a heart to guide the CSD in an extended state, each primary elongate member being distally and proximally movable with respect to the body between retracted and extended states; and
        an array of secondary members, each secondary member slidably attached to and guided by an associated primary elongate member to releasably support the CSD and slide the CSD over the heart, wherein each secondary member is distally and proximally movable with respect to its associated primary elongate member between retracted and extended states; and
        an actuating system on the body for moving the deployment mechanism between the retracted and extended states, the actuating system comprising;
        at least one primary actuating mechanism coupled to an associated primary elongate member; and
        at least one secondary actuating mechanism coupled to an associated secondary member,
        wherein the at least one primary actuating mechanism is configured to move its associated primary elongate member distally and proximally with respect to others of the array of primary elongate members; and
        wherein the at least one second actuating mechanism is coupled to an associated secondary member and configured to move the associated secondary member distally and proximally with respect to its associated primary elongate member.

2. The apparatus of claim 1, wherein the actuating system further comprises a first handle coupled to the array of primary elongate members, wherein the at least one primary actuating mechanism is movably coupled to the first handle, and wherein the first handle moves the array of primary elongate members between retracted and extended states.

3. The apparatus of claim 1, wherein the apparatus is configured to house and deliver a CSD comprising a cardiac jacket for reducing tension in the heart wall by constraining or resisting expansion of the heart.

4. The apparatus of claim 1, wherein the array of primary elongate members is elliptical or an irregular shape configured to conform to an atrioventricular groove of the heart.

5. The apparatus of claim 1, wherein the deployment mechanism is rotatable independently of the body about a longitudinal axis of the body.

6. The apparatus of claim 1, further comprising an epicardial stabilization device mechanically attached to an upper surface of the body, wherein the epicardial stabilization device is configured to grasp and engage heart tissue to stabilize the heart during delivery of the CSD.

* * * * *